United States Patent
Carr

[19]

[11] Patent Number: 5,891,107
[45] Date of Patent: Apr. 6, 1999

[54] DISCRETE PERSONAL HYGIENE SYSTEM

[76] Inventor: Robert C. Carr, 29659 Sierra Point Cir., Farmington Hills, Mich. 48331-1479

[21] Appl. No.: 844,360

[22] Filed: Apr. 18, 1997

[51] Int. Cl.[6] .................................................. A61M 5/00
[52] U.S. Cl. ............................................ 604/259; 604/275
[58] Field of Search ................................. 604/259, 261, 604/262, 264, 279, 239, 275

[56] References Cited

U.S. PATENT DOCUMENTS

| | | |
|---|---|---|
| 586,679 | 7/1897 | Woolley .............................. 604/259 X |
| 703,616 | 7/1902 | Schwartz ................................. 604/259 |
| 920,225 | 5/1909 | Denburgh et al. . |
| 1,546,940 | 7/1925 | Pennington .............................. 604/275 |
| 2,392,085 | 1/1946 | Ferrel ..................................... 604/275 |
| 2,515,413 | 7/1950 | Mansfield . |
| 2,554,362 | 5/1951 | Ferguson . |
| 2,644,451 | 7/1953 | Sokolik .................................. 604/279 |
| 2,672,869 | 3/1954 | Manville . |
| 2,880,864 | 4/1959 | Russo . |
| 2,997,161 | 8/1961 | Bass . |
| 3,100,487 | 8/1963 | Bathish . |
| 3,131,812 | 5/1964 | Constant . |
| 3,219,402 | 11/1965 | Holman . |
| 3,384,231 | 5/1968 | Cox et al. . |
| 3,524,690 | 8/1970 | Gurney . |
| 3,854,479 | 12/1974 | Duke . |
| 3,916,896 | 11/1975 | Ballard ............................... 604/279 X |
| 3,990,448 | 11/1976 | Mather et al. .......................... 604/275 |
| 4,842,580 | 6/1989 | Ovelette ................................. 604/275 |

*Primary Examiner*—John D. Yasko
*Attorney, Agent, or Firm*—Harness, Dickey & Pierce, P.L.C.

[57] ABSTRACT

A personal hygiene system includes a cabinet, a cover hingedly attached to said cabinet, a fluid bottle removably attachable to the cabinet, a hose attached to the fluid bottle, and at least one personal hygiene accessory attached to said hose. A plurality of flexible tabs are formed on the back side of the interior of the cabinet for releasably holding the fluid bottle. Optionally, a quick-connector release may be used to connect the hose and the fluid bottle. A plurality of tabs are provided in an array about the fluid bottle for releasably receiving the tube. One or more holders are preferably formed on the back wall of the cabinet for releasably receiving a personal hygiene accessory.

19 Claims, 2 Drawing Sheets

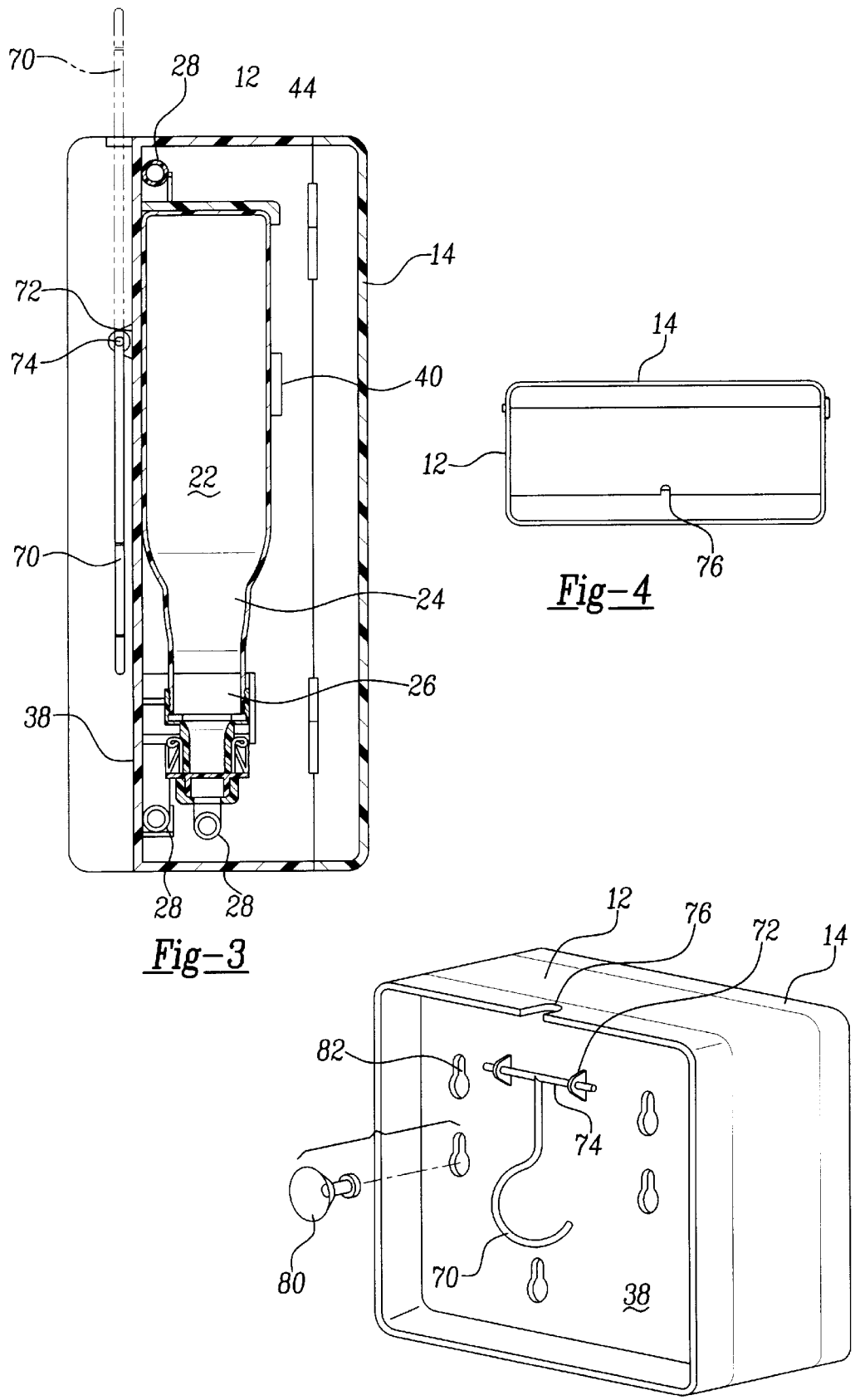

DISCRETE PERSONAL HYGIENE SYSTEM

BACKGROUND OF THE INVENTION

I. Field of the Invention

The present invention relates to a system for personal hygiene for both men and women. More particularly, the present invention relates to a system for human hygiene which includes a solution container, a fluid tube connected to the solution container, fittings for attachment to the tube, and a housing for discrete and convenient holding all of these components.

II. Description of the Prior Art

It is occasionally desirable for a person to apply a cleansing or medicinal solution either rectally or vaginally as required for the proper maintenance of hygiene. When delivered rectally, such solutions (typically enema solutions) are applied for the purpose of maintaining proper bowel condition. When delivered vaginally, such solutions are applied for the purpose of cleansing. Known systems typically comprise a solution bag, having a solution outlet, a flexible tube connected to the solution outlet, a solution delivery nozzle connected to the flexible tube, and a solution control valve.

A variety of approaches have been taken in efforts to improve personal hygiene systems. Examples of such efforts are embodied in the following patents: U.S. Pat. No. 3,254,479, issued Dec. 17, 1974, to Pulse for DEVICE FOR ADMINISTERING AN ENEMA; U.S. Pat. No. 3,524,690, issued Aug. 18, 1970, to Gurzney for HYGIENE KIT AND CASE; U.S. Pat. No. 3,384,231, issued May 21, 1968, to Cox et al., for FOLDING SYRINGE CASE AND CONTAINER; U.S. Pat. No. 3,219,402, issued Nov. 23, 1965, to Holman for CASINGS; U.S. Pat. No. 3,131,812, issued May 5, 1964, to Constant for HYGIENIC SYRINGE DEVICES; U.S. Pat. No. 3,100,487, issued Aug. 13, 1963, to Bathish for APPARATUS FOR ADMINISTERING LIQUIDS; U.S. Pat. No. 2,997,161, issued Aug. 22, 1961, to Bass for SANITARY BAG; U.S. Pat. No. 2,880,864, issued Apr. 7, 1959, to Russo for ACCESSORY CONTAINER; U.S. Pat. No. 2,672,869, issued Mar. 23, 1954, to Manville for SYRINGE; U.S. Pat. No. 2,554,362, issued May 22, 1951, to Ferguson for BATHROOM CABINET OR THE LIKE; and U.S. Pat. No. 2,515,413, issued on Jul. 18, 1950, to Mansfield for CAMOUFLAGED SYRINGE CONTAINER.

While originally products incremental improvements in the state of the prior art of these patents fail to provide a desired improvement of combining discreetness with convenience. In the hospital setting, the need for discreetness is generally important given the function of the setting. However, at the home setting, the need for discreetness coupled with convenience is paramount. The individual concerned with discretion is unlikely to mount a non-discrete syringe system in a place of convenience, thus compromising the value of having the system in the first place.

Accordingly, a discrete and convenient hygiene system for use by both men and women remains wanting.

SUMMARY OF THE INVENTION

Accordingly, it is the general object of the present invention to provide a personal hygiene system which overcomes the disadvantages of the prior art.

More particularly, it is an object of the present invention to provide a personal hygiene system which is convenient to use.

It is a further object of the present invention to provide such a system which may be readily supported by either fastening to an upright surface or by hanging from a rod.

Yet a further object of the present invention is to provide such a system which includes a cabinet and a cover hingedly attached to the door for rendering the device relatively discrete.

Still a further object of the present invention is to provide such a system in which the hose may be readily stored.

A further object of the present invention is to provide such a system in which one or more accessories may be releasably situated inside of the cabinet.

An additional object of the present invention is to provide such a system which optionally incorporates a quick-release assembly for providing releasable attachment of the hose to the fluid bottle.

Yet still an additional object of the present invention is to provide such a system which has a fluid control valve conveniently situated on the hose.

These and other objects of the present invention are provided in a personal hygiene system which includes a cabinet, a cover hingedly attached to said cabinet, a fluid bottle removably attachable to the cabinet, a hose attached to the fluid bottle, and at least one personal hygiene accessory attached to said hose. A plurality of opposed tabs are formed on the back wall of the cabinet in an array around the fluid bottle to provide maximum convenience to the user. In addition, a plurality of flexible tabs are formed on the back side of the interior of the cabinet for releasably holding the fluid bottle. Optionally, a quick-connector release may be used to connect the hose and the fluid bottle.

A plurality of tabs are provided in an array about the fluid bottle for releasably receiving the tube. One or more holders are preferably formed on the back wall of the cabinet for releasably receiving a personal hygiene accessory. The cabinet may either be mounted on an upright surface through the use of one or more suction cups or may be suspended from a rod by use of a hanger.

Other objects and advantages of the present invention will become apparent as the description proceeds below.

BRIEF DESCRIPTION OF THE DRAWINGS

The present invention will be more fully understood by reference to the following detailed description of the preferred embodiments of the present invention when read in conjunction with the accompanying drawings, in which like reference characters refer to like parts throughout the views, and in which:

FIG. 3 is a sectional view of the apparatus of FIGS. 1 and 2 taken along line 3—3 of FIG. 2;

FIG. 4 is a top view of the apparatus of the present invention shown with the cover in its closed position; and FIG. 5 is a perspective view of the back and one of the sides of the personal hygiene apparatus according to the present invention.

DETAILED DESCRIPTION OF THE PREFERRED EMBODIMENT

The drawings disclose the preferred embodiment of the present invention. While the configurations according to the illustrated embodiment are preferred, it is envisioned that alternate configurations of the present invention may be adopted without deviating from the invention as portrayed. The preferred embodiment is discussed hereafter.

Figure 1:
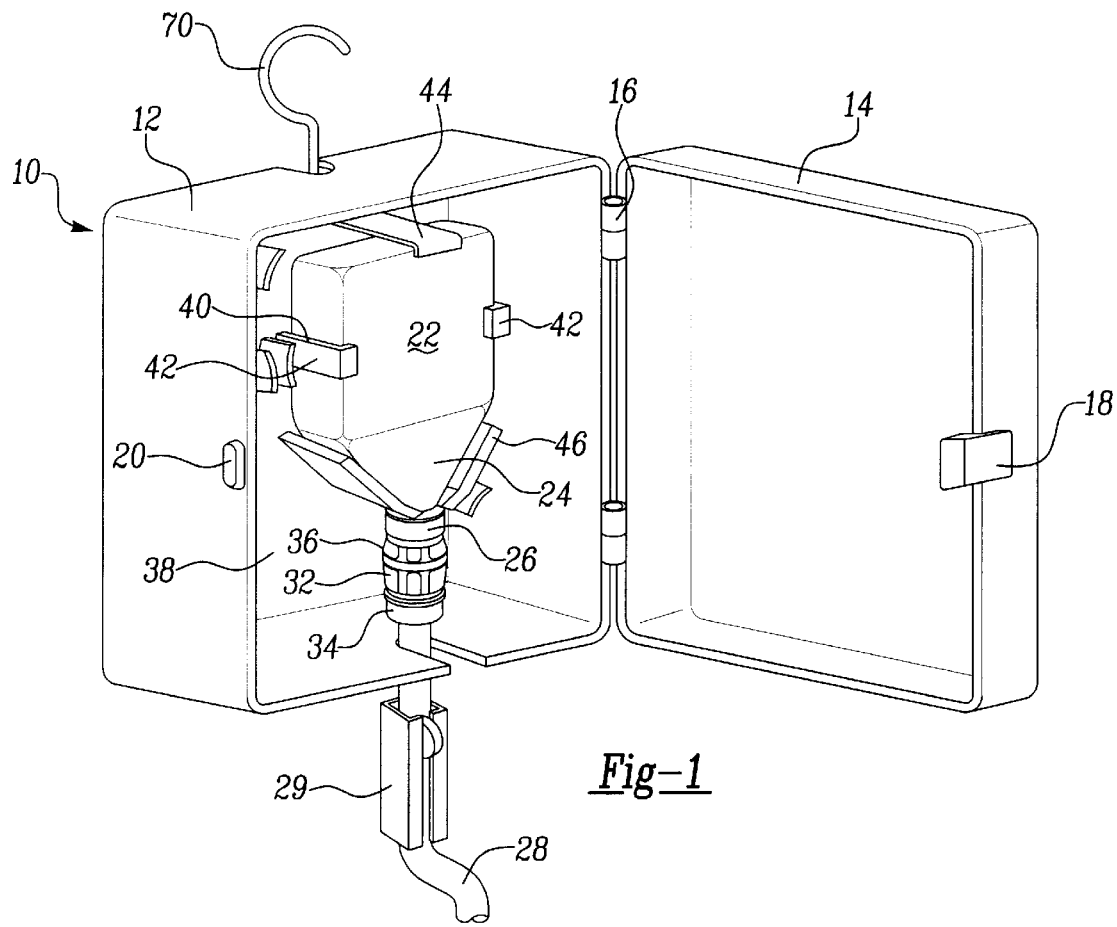
FIG. 1 is a perspective view of the personal hygiene apparatus according to the present invention shown in its open position.
Figure 2:
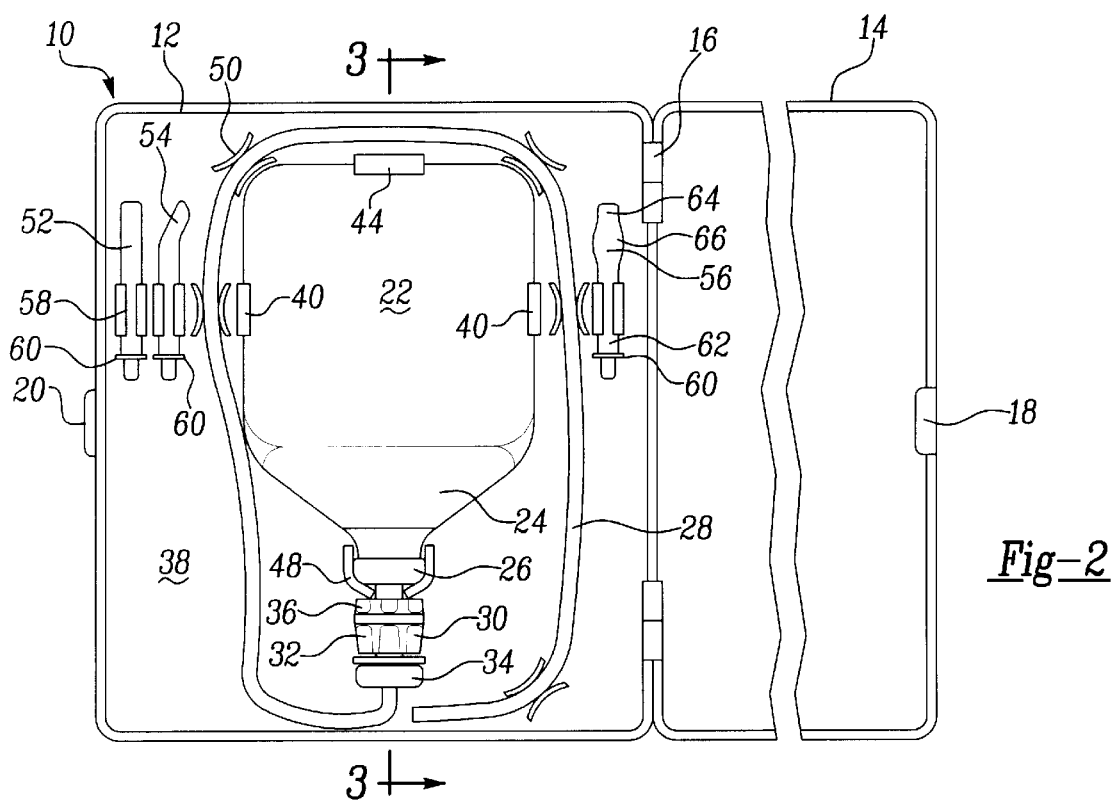
FIG. 2 is raised elevational view of the personal hygiene apparatus shown in FIG. 1, but illustrating the components of the apparatus shown therein.

Referring to FIGS. 1 and 2, two related views of a personal hygiene apparatus, generally illustrated as 10, are shown with the apparatus 10 being in its open position. The apparatus 10 includes a cabinet 12 and a cover 14 hingedly attached to the cabinet 12 by means of one or more hinge assemblies 16. A latch 18 is formed on the cover 14 for releasable engagement with a catch 20 formed on the cabinet. Preferably both the cabinet 12 and the cover 14 are composed of a resilient, polymerized material which provides lightweight construction, as well as easy cleaning and lower production costs.

Releasably housed within the apparatus 10 is a fluid bottle 22. The fluid bottle 22 is also preferably composed of a resilient polymerized material for easy care. In addition, the bottle 22 is preferably composed of such a material that is dishwasher safe, thereby providing the user with an easy way of cleaning. In addition, the material of the fluid bottle 22 must be capable of resisting any chemical reaction which might reasonable be expected to be otherwise possible given the contained fluid. The shape of the bottle is such that it includes a lower end, generally illustrated as 24, which is V-shaped in configuration so as to maximize flow and provide for the complete emptying of the contents of the bottle 22 when desired. The bottle 22 also includes a neck 26 at the terminal end of the lower end 24.

A flexible hose 28 is provided for directing the fluid from the bottle 22 to the point of use. The flexible hose 28 may be composed of any one of a variety of plastics capable of withstanding repeated bending and cleaning. In addition, and like the fluid bottle 22, the material of the flexible hose 28 must be capable of resisting any chemical interaction with the constrained fluid. The length of the hose 28 is according to that preferred for proper use. A flow regulator valve 29 is provided to selectively regulate the amount of fluid passing through the hose 28. The regulator valve 29 may be of the "on-off" type or may be such that the amount of flow can be selectively adjusted by the user.

The fluid hose 28 is connected to the neck 26 of the bottle 22. Connection may be made by a variety of methods, but a preferred method is through the use of a quick-connect type of connector, generally shown as 30. The connector 30 includes a releasing portion 32 and a releasable portion 34. The releasing portion 32 is operable to release the releasable portion 34 by axially moving a sleeve 36 away in a direction away from the releasable portion.

The cabinet 12 includes a back wall 38. The fluid bottle 22 is releasably positioned within the cabinet 12 and is held in place against the back wall 38 by a series of flexible tabs. The format of these tabs may be varied. For example, the embodiments of FIGS. 1 and 2 share in common a pair of opposed side tabs 42 and a top tab 44. The side tabs 42 and the top tab 44 are flexible enough so as to allow release of the bottle 22 therefrom if translated against an inherent resistive force away from the bottle 22 and away from their illustrated holding position. Of course, a greater or lesser number of tabs 42 and 44 may be used other than as illustrated.

At least two approaches may be taken for holding the lower end 24 of the bottle 22. The first is illustrated in FIG. 1 and shows the use of a pair of opposed tabs 46 which are formed on the wall 38 so as to support the lower end 24 directly. The second is illustrated in FIG. 2 and shows the use of a pair of opposed tabs 48 which are also formed on the wall 38 so as to support the neck 26. It is, of course, possible that the opposed tabs 46 and the opposed tabs 48 may be used in the same construct of the present invention for providing maximum support.

For maximum convenience and to allow the apparatus 10 to be used discretely, the tube 28 is entirely disposable within the cabinet 12 when not in use. FIG. 2 best illustrates the tube 28 having been wrapped about the bottle 22 in a generally coiled fashion. The tube 28 is held in place by a series of pairs of opposed tabs 50. As illustrated, each member of the pairs of tabs 50 is defined by a curved formation, such that the curves of the pairs of tabs are positioned so as to releasably engage the tube 28.

To operate the apparatus 10, it is necessary for the user to attach a preferred accessory tip to the fluid outlet end of the tube 28 as desired for the particular use in mind. Illustrated in FIG. 2 are a number of accessories, including a straight tip 52, an angled tip 54, and a bulged tip 56. Each of the tips 52, 54, and 56 is releasably held to the back wall 38 of the cabinet 12 by a number of flexible tabs 58. In addition, each of the tips 52, 54, and 56 includes a flange 60 which limits the depth to which the tube-engaging end of the tips may be inserted into the tube 28.

The tip 56 includes a proximal end 62 and a distal end 64. As may be understood by reference to the illustration of FIG. 2, the tip 56 (as well as the tips 52 and 54) generally defines a tube. The proximal end 62 of the tip 56 is generally of the same diameter as the distal end 64. Formed between the proximal end 62 and the distal end 64 is a bulge 66. The tip 56 is particularly adapted for insertion into the user's anus, and the bulge 66, once passed by the sphincter muscles, helps to retain the tip 56 in its desired position until use of the apparatus 10 is completed. After use, of course, the bottle 22, the tube 28, and one or more of the tips 52, 54, and 56 should be washed thoroughly in a known manner to prepare the apparatus for later use.

To provide maximum convenience to the operator using the apparatus 10, it is desirable to position or otherwise suspend the apparatus 10 in a place convenient to the user. Accordingly, a variety of methods are proposed for such positioning. FIGS. 3 through 5 illustrate the various approaches taken to provide such a support system.

FIG. 3 is a sectional view of the apparatus 10 taken along line 3—3 of FIG. 2. FIG. 4 is a top view of the apparatus 10 of the present invention shown with the cover 14 in its closed position, while FIG. 5 is a perspective view of the back and one of the sides of the personal hygiene apparatus 10.

The apparatus 10 includes a hanger 70 for suspending the unit from a pole or hook (neither shown). The hanger is connected to the recessed outer side of the back wall 38 by a flange 72. A rod 74 pivotally connects the hanger 70 to the flange 72. The hanger 70 is movable from a stowed position when not in use as illustrated in FIG. 5 and, in solid lines, in FIG. 3. A notch 76 is formed in the top wall of the cabinet 12 to provide for convenient placement of the hanger 70 therethrough when the hanger 70 is in use.

As an alternative to suspending the apparatus 10 from a rod or a hood, means are provided to attach the unit to an upright smooth surface such as a bathroom cabinet. Such means are defined as one or more suction cups 80 which are slottingly fitted into a like number of key-hole slots formed in the back wall 38. When in place, the cup portion of the suction cup 80 extends beyond the cabinet walls to allow for attachment to the upright surface.

When not in use, the apparatus 10 may be hung on a rod, a hook, or the like or may be positioned against the upright surface. With the cover 14 closed, the apparatus 10 is highly discrete. When in use, the user simply opens the cover 14, removes and unwinds the tube 28, selects and attaches the appropriate tip 52, 54, or 56, inserts the selected tip as desired, and operates the flow regulator valve 29 to achieve the desired level of flow. Once completed, the regulator valve 29 is moved to its closed position, and the bottle 22, the tube 28, and the selected tip are disassembled and cleaned for the next use.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

What is claimed is:

1. A personal hygiene apparatus comprising:
    a cabinet, said cabinet having a back wall;
    a cover hingedly attached to said cabinet;
    a fluid bottle positionable within said cabinet, said fluid bottle having a front side and a lower end;
    at least a pair of opposed flexible flanges for holding said fluid bottle in said cabinet, each of said flanges having a tab for engagement with said front side of said fluid bottle;
    means for supporting said lower end of said fluid bottle;
    a flexible hose attached to said lower end of said bottle;
    a plurality of hose-holding clips formed on said back wall of said wall;
    at least one personal hygiene accessory for releasable attachment to said hose; and
    means formed on said back wall for holding said at least one personal hygiene accessory.

2. The personal hygiene apparatus of claim 1, wherein said hose-holding clips are defined by a plurality of pairs of opposed tabs formed on said back wall.

3. The personal hygiene apparatus of claim 2, wherein said plurality of pairs of opposed tabs are formed in an array around said fluid bottle.

4. The personal hygiene apparatus of claim 3, wherein each member of said pair of tabs is defined by a curved wall, each member of said pair opposing an adjacent member such that a narrow channel is formed between said curved walls within which at least a portion of said hose is releasably placeable.

5. The personal hygiene apparatus of claim 1, wherein at least one of said accessories is defined by a tube, said tube having a distal end having a diameter and a proximal end having a diameter, said diameters being substantially identical, said proximal end being releasably attachable to said hose, said tube having an outward bulge formed between said proximal and distal ends.

6. The personal hygiene apparatus of claim 1, wherein said lower end of said fluid bottle defines a V-shape and wherein said means for supporting said lower end of said fluid bottle is defined by a pair of spaced-apart, substantially flat tabs that extend from said back wall.

7. The personal hygiene apparatus of claim 1, wherein said lower end of said fluid bottle includes a neck and wherein said means for supporting said lower end of said fluid bottle is defined by a pair of spaced-apart curved tabs which extend from said back wall.

8. The personal hygiene apparatus of claim 1, further including a quick-connect assembly between said lower end of said fluid bottle and said hose for releasably mating said fluid bottle and said hose.

9. The personal hygiene apparatus of claim 1, further including a fluid shut-off valve positioned on said hose.

10. The personal hygiene apparatus of claim 1, wherein said back wall includes an outer back side and wherein said apparatus further includes a suction cup for attaching said cabinet to a smooth surface.

11. The personal hygiene apparatus of claim 1, wherein said back wall includes an outer back side and wherein said apparatus further includes a hanger for attaching said cabinet to a rod.

12. The personal hygiene apparatus of claim 11, wherein said outer back side is recessed.

13. The personal hygiene apparatus of claim 11, wherein said hanger is rotatable between an extended position for hanging to a stowed position for storing.

14. The personal hygiene apparatus of claim 13, wherein said cabinet includes a top wall and said top wall includes a notch formed therein for accommodating said hanger when unfolded to its extended position.

15. A personal hygiene apparatus comprising:
    a cabinet including a wall;
    a fluid bottle;
    means for releasably attaching said fluid bottle to said wall;
    a fluid-delivery hose connected to said fluid bottle;
    a plurality of hose-holding clips formed on said back wall of said wall, said hose-holding clips being defined by a plurality of pairs of opposed tabs formed on said back wall, said plurality of pairs of opposed tabs being formed in an array around said fluid bottle, each member of said pair of tabs being defined by a curved wall, each member of said pair opposing an adjacent member such that a narrow channel is formed between said curved walls within which at least a portion of said hose is releasably placeable.

16. The personal hygiene apparatus of claim 15, wherein at least one of said accessories is defined by a tube, said tube having a distal end having a diameter and a proximal end having a diameter, said diameters being substantially identical, said proximal end being releasably attachable to said hose, said tube having an outward bulge formed between said proximal and distal ends.

17. The personal hygiene apparatus of claim 16, wherein said fluid bottle has a front side, said apparatus further including at least a pair of opposed flexible flanges for holding said fluid bottle in said cabinet, each of said flanges having a tab for engagement with said front side of said fluid bottle.

18. The personal hygiene apparatus of claim 17, wherein said fluid bottle has a lower end and wherein said apparatus includes means for supporting said lower end.

19. A personal hygiene apparatus comprising:
    a cabinet, said cabinet having a back wall;
    a cover hingedly attached to said cabinet;
    a fluid bottle removably positionable within said cabinet, said fluid bottle having a front side and a lower end;
    at least a pair of opposed members for holding said fluid bottle in said cabinet, each of said members being engageable with said front side of said fluid bottle;
    means for supporting said lower end of said fluid bottle;
    a flexible hose attached to said lower end of said bottle;
    means for retaining said hose within said cabinet;
    at least one personal hygiene accessory for releasable attachment to said hose; and
    means associated with said cabinet for holding said at least one personal hygiene accessory.

* * * * *